(12) United States Patent
Wolford

(10) Patent No.: US 7,118,575 B2
(45) Date of Patent: Oct. 10, 2006

(54) CHIP BREAKERS FOR ORTHOPAEDIC REAMERS

(75) Inventor: Todd Wolford, Goshen, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 560 days.

(21) Appl. No.: 10/348,932

(22) Filed: Jan. 22, 2003

(65) Prior Publication Data

US 2004/0143271 A1 Jul. 22, 2004

(51) Int. Cl.
*A61B 17/00* (2006.01)

(52) U.S. Cl. .................................................. 606/80

(58) Field of Classification Search .. 623/22.21–22.39; 606/79–81
See application file for complete search history.

(56) References Cited

U.S. PATENT DOCUMENTS

| | | |
|---|---|---|
| 4,023,572 A * | 5/1977 | Weigand et al. ............... 606/81 |
| 4,811,632 A | 3/1989 | Salyer |
| 5,116,165 A | 5/1992 | Salyer |
| 5,203,653 A | 4/1993 | Kudla |
| 5,376,092 A | 12/1994 | Hein et al. |
| 5,462,548 A | 10/1995 | Pappas et al. |
| 5,709,688 A | 1/1998 | Salyer |
| 5,879,405 A | 3/1999 | Ries et al. |
| 5,968,049 A | 10/1999 | Da Rold |
| 6,001,105 A | 12/1999 | Salyer |
| 6,027,503 A | 2/2000 | Khalili et al. |
| 6,106,536 A | 8/2000 | Lechot |
| 6,168,600 B1 * | 1/2001 | Grace et al. ................... 606/81 |
| 6,221,076 B1 | 4/2001 | Albrektsson et al. |
| 2003/0135219 A1 * | 7/2003 | Salyer et al. ................... 606/81 |

\* cited by examiner

*Primary Examiner*—Eduardo O. Robert
*Assistant Examiner*—Michael J. Araj
(74) *Attorney, Agent, or Firm*—Taylor & Aust, P.C.

(57) ABSTRACT

An orthopaedic reamer, including a generally hemispherical shell having a plurality of tongues. Each tongue partially defines a corresponding C-shaped opening with a substantially constant width. Each tongue includes a cutting segment. The cutting segment includes at least one notch and a plurality of cutting teeth. Adjacent cutting teeth are separated by a corresponding notch.

11 Claims, 2 Drawing Sheets

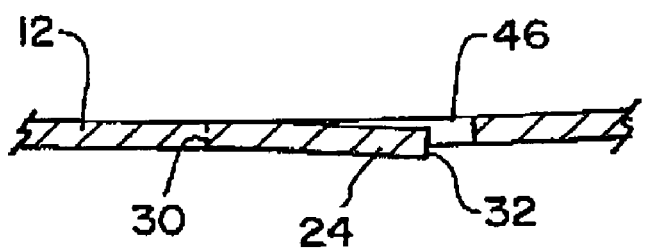
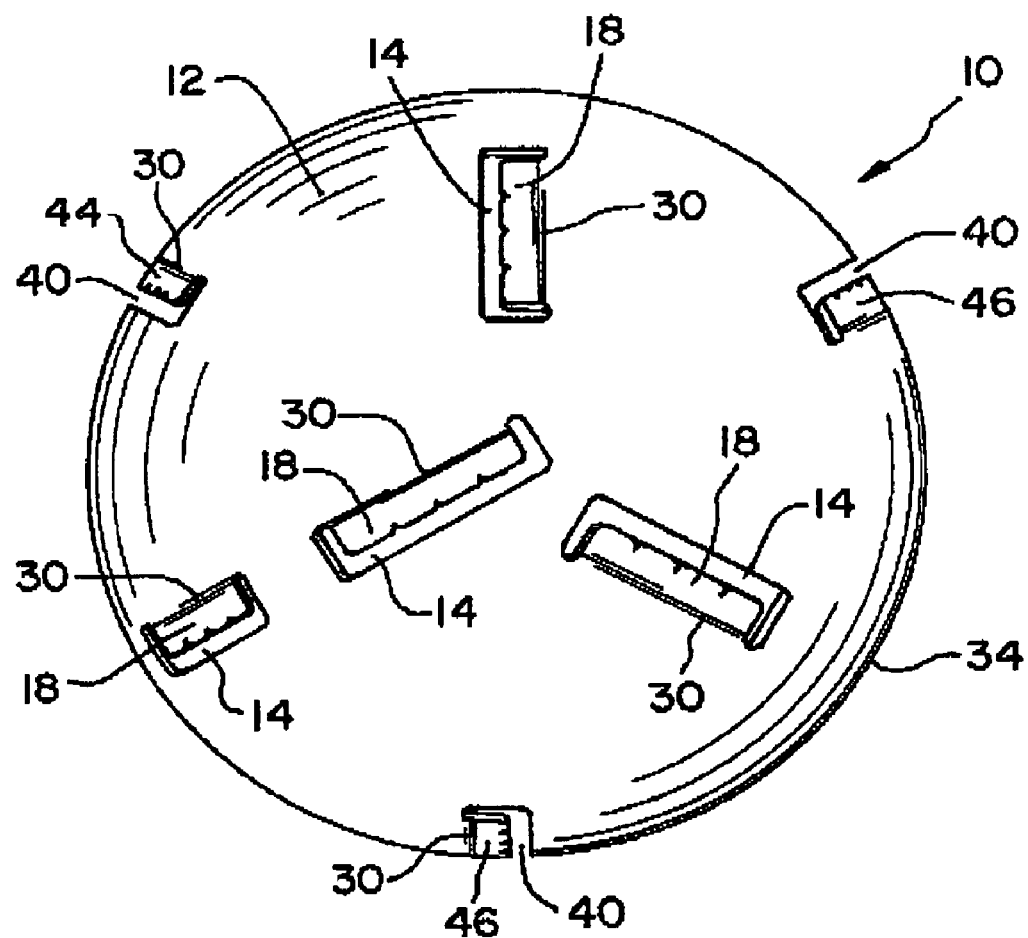

CHIP BREAKERS FOR ORTHOPAEDIC REAMERS

BACKGROUND OF THE INVENTION

1. Field of the Invention

The present invention relates to orthopaedic reamers, and, more particularly, to chip breaker cutting apertures and surfaces for orthopaedic reamers.

2. Description of the Related Art

A hip joint prosthesis requires preparation of the acetabulum by milling a precision shape therein using an orthopaedic reamer. A typical orthopaedic reamer has a hollow hemispherical shell shape with apertures in the hemispherical shell. The hemispherical shell is attached to a driver with a shaft which can be inserted into a rotating tool such as a drill thereby providing rotation of the orthopaedic reamer, and hence, the motive force for the milling operation. The apex of the hemispherical shell typically is along the shaft longitudinal axis.

The apertures in the hemispherical shell have a dual purpose. Firstly, an edge of each aperture is formed outwardly, respective to the shell center, to form a cutting tooth or cutting surface. The forming of the aperture edge outwardly is referred to as a lipping operation. Secondly, the apertures allow milled tissue to collect in the shell interior, thereby providing a somewhat self-cleaning aspect to the milling operation. The apertures and cutting surfaces are located on the shell to provide approximately 180° cutting coverage during rotation of the acetabular reamer thereby allowing a uniform milling of the acetabulum.

The size, shape, quantity and location of apertures and corresponding cutting surfaces are interrelated. For example, smaller geometry apertures and corresponding cutting surfaces require a greater quantity in the hemispherical shell to provide approximately 180° cutting coverage during rotation of the acetabular reamer. Conversely, fewer relatively large size apertures and corresponding cutting surfaces are required to provide the same cutting coverage. The size and shape of the cutting apertures also influences the location of the apertures. For example, one known design of acetabular reamer has approximately 0.2 inch diameter round aperatures arranged in a spiral pattern in the reamer hemispherical shell.

When the reamer is used to prepare the acetabulum for hip joint prosthesis, variation in the size of the acetabulum for the human population requires a range of sizes of acetabular reamers, a specific size of the acetabular reamer being determined by the hip joint size of the person undergoing hip joint prosthesis. The different sizes of acetabular reamers are generally specified by different radii of curvature, or diameters, of the hemispherical shell. For a given size and shape for apertures and corresponding cutting surfaces, a larger reamer size requires a larger quantity, and possibly different locations.

Manufacturing cost for a reamer is incremented for additional apertures and corresponding cutting surfaces; therefore, larger and fewer cutting apertures save manufacturing cost. When the reamer is used to prepare the acetabulum for hip joint prosthesis, a rotary hand tool provides the motive force and is connected to a driver which is connected to a reamer. In use, larger cutting surfaces remove more material for a given rotation of the tool leading to vibration or chattering. This vibration or chattering can degrade cutting performance by making the rotary tool-driver-reamer combination harder for the operator (surgeon) to control. Smaller cutting surfaces remove smaller pieces of material, thereby improving the vibration characteristics of the rotary tool-driver-reamer combination, but require a larger quantity of cutting surfaces, thereby increasing the manufacturing cost of the reamer. In other words, there is a trade-off between the manufacturing efficiency of fewer, larger cutting apertures and the cutting and vibration performance of a greater number of, and smaller, cutting apertures.

What is needed in the art are reamer apertures and corresponding cutting surfaces with the manufacturing efficiency of larger cutting apertures and the cutting, chip breaking and vibration performance of smaller cutting apertures.

SUMMARY OF THE INVENTION

The present invention provides orthopaedic reamer cutting surfaces with notches separating the cutting teeth. Each cutting tooth has a cutting surface associated with a corresponding C-shaped opening with a substantially constant width.

The invention comprises, in one form thereof, an orthopaedic reamer including a generally hemispherical shell having a plurality of tongues. Each tongue partially defines a corresponding C-shaped opening with a substantially constant width. Each tongue includes a cutting segment. The cutting segment includes at least one notch and a plurality of cutting teeth. Adjacent cutting teeth are separated by a corresponding notch.

An advantage of the present invention is an orthopaedic reamer with apertures and corresponding cutting surfaces having the manufacturing efficiency of larger cutting apertures.

Another advantage is an orthopaedic reamer with larger cutting apertures and the cutting, chip breaking and vibration performance of smaller cutting apertures.

Yet another advantage is the general shape of the C-shaped opening lends itself to modem efficient machining processes further improving the production efficiency of the orthopaedic reamer.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 3 is a cross-sectional view taken along section line 3—3 in FIG. 2; and

FIG. 4 is a top view of the orthopaedic reamer shown in FIG. 1.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
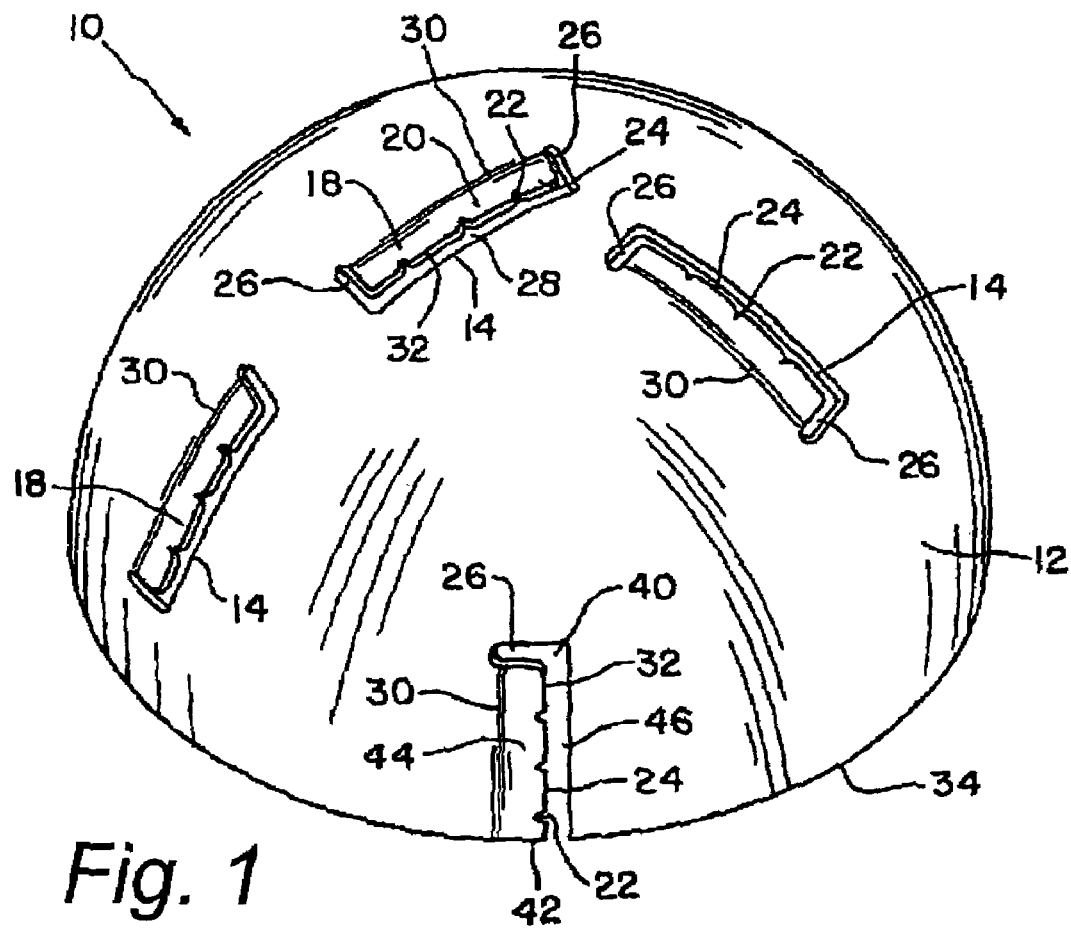
FIG. 1 is a perspective view of an embodiment of an orthopaedic reamer of the present invention.

Referring now to the drawings, and more particularly to FIG. 1, there is shown an orthopaedic reamer 10 which generally includes hemispherical shell 12 having a plurality of C-shaped openings 14 and a plurality of tongues 18.

C-shaped opening 14 include release slots 26 and cutting aperture 28. Release slots 26 and cutting apertures 28 have a substantially constant width. Release slots 26 allow the forming of tongue 18 outward from hemispherical shell 12 at bend 30. The angle between release slots 26 and cutting aperture 28 is approximately 90°, however, other angles varying from 0° to 180° are possible. Alternatively, release slots 26 and cutting aperture 28 can form a continuously curved C-shaped openings 14. C-shaped openings 14 can alternatively include a plurality of release slots 26 located at either end of cutting aperture 28. C-shaped openings 14 are located on hemispherical shell 12 to provide approximately 180° cutting coverage during rotation of the orthopaedic reamer 10 thereby allowing a uniform milling of, for example, an acetabulum.

Tongue 18 includes cutting segment 20. Each tongue 18, along with hemispherical shell 12, defines a corresponding C-shaped opening 14 therebetween. Cutting segment 20 includes at least one notch 22 and a plurality of cutting teeth 24. Adjacent cutting teeth 24 are separated by a corresponding notch 22. Notch 22 can be a variety of shapes including at least partially rectangular, triangular, polygonal, circular, parabolic, elliptical, a combination of curved segments and/or a combination of curved and straight segments. The width of notch 22 is less than the width of tooth 24.

In order to provide 180° cutting coverage during rotation of the orthopaedic reamer 10, L-shaped openings 40 are provided proximate to hemisphere base 34. L-shaped openings 40 are similar to C-shaped opening 14 with the exception that release edge 42 in L-shaped openings 40 replaces one of release slots 26. Each L-shaped opening 40 is essentially a partial C-shaped opening 14 with second tongue 44 essentially a partial tongue 18 and second cutting aperture 46 a partial cutting aperture 28. The angle between release edge 42 and second cutting aperture 46 is approximately 90°; however, other angles varying from 0° to 180° are possible. The angle between release slots 26 and cutting aperture 46 is approximately 90°; however, other angles varying from 0° to 180° are possible. L-shaped openings 40 are necessitated, in part, by the requirement that during rotation of orthopaedic reamer 10, any notch 22 must be overlapped by at least one cutting tooth. This requirement eliminates grooves in the machined element (not shown) such as an acetabulum. For a given radius for hemispherical shell 12 and a given size for C-shaped opening 14, placement of C-shaped openings 14 to provide 180° cutting coverage during rotation of the orthopaedic reamer 10 results in partial C-shaped openings near hemisphere base 34, hence the L-shaped openings 40 in orthopaedic reamer 10. Depending on the position of L-shaped opening or openings 40 on hemispherical shell 12, a corresponding cutting segment can include a single tooth or partial tooth with no corresponding notch.

The alternate shapes of notch 22 described above can result in alternate shapes of cutting segment 20, such as a wave shape.

Referring to FIG. 3, cutting edge 32 is formed during the fabrication of C-shaped opening 14 or L-shaped opening 40, and further during the forming of tongue 18 or second tongue 44 outward from hemispherical shell 12. Cutting edge 32 can be a variety of cross-sectional shapes including at least partially rectangular, triangular, polygonal, circular, parabolic, elliptical, a combination of curved segments and/or a combination of curved and straight segments.

In use, orthopaedic reamer 10 is attached to a driver (not shown) with a shaft which can be inserted into a rotating tool (not shown) such as a drill thereby providing rotation of orthopaedic reamer 10. An operator (a surgeon, not shown) uses orthopaedic reamer 10 to prepare an orthopaedic element of the patient (not shown). If the operation is hip joint prosthesis, the acetabulum (not shown) is prepared by milling a precision shape therein using orthopaedic reamer 10.

Figure 2:
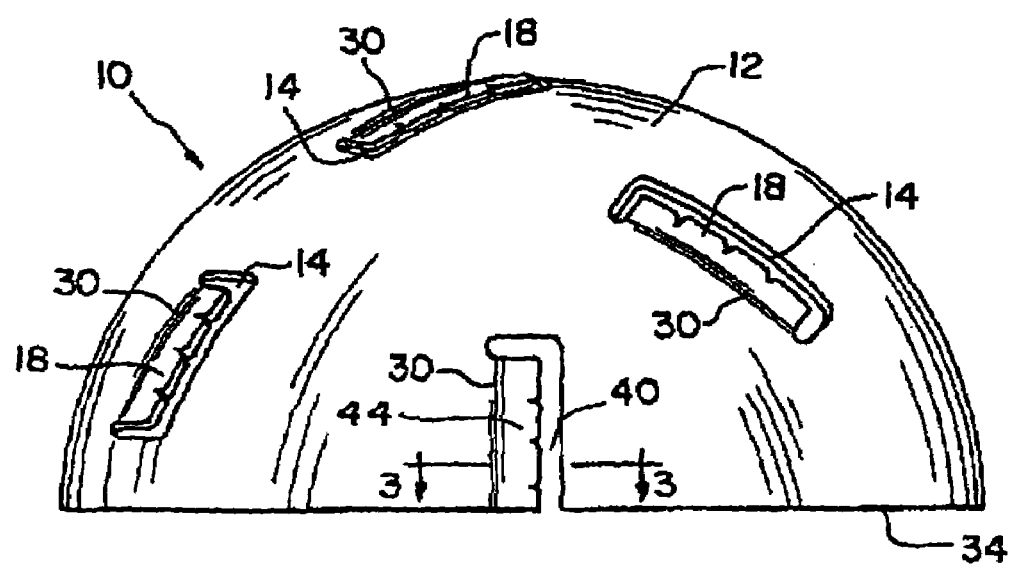
FIG. 2 is a side view of the orthopaedic reamer shown in FIG. 1.

As can be best seen in FIGS. 1, 2 and 4, the relatively large size of C-shaped opening 14 and L-shape opening 40 allows for fewer such openings in hemispherical shell 12, thereby reducing manufacturing costs for orthopaedic reamer 10. The relatively large cutting segment 20 is separated into a plurality of smaller cutting teeth 24 and corresponding notch or notches 22 thereby breaking removed material into smaller chips and giving orthopaedic reamer 10 the cutting, chip breaking and vibration performance of smaller cutting apertures and surfaces. The general shape of C-shaped opening 14 and L-shape opening 40 lends itself to modem efficient machining processes further improving the production efficiency of orthopaedic reamer 10.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising: a generally hemispherical shell, including a plurality of first tongues, each said first tongue partially defining a corresponding C-shaped opening with a substantially constant width, each said first tongue including a cutting segment, said cutting segment including at least one notch and a plurality of cutting teeth, adjacent said cutting teeth separated by a corresponding said notch; and at least one second tongue, each said second tongue partially defining a corresponding said L-shaped opening with a substantially constant width, each said second tongue including a cutting segment, said cutting segment including at least one notch and a plurality of cutting teeth, adjacent said cutting teeth separated by a corresponding said notch.

2. The orthopaedic reamer of claim 1, wherein said C-shaped opening includes a plurality of release slots and a cutting aperture therebetween.

3. The orthopaedic reamer of claim 2, including an angle of approximately 90° between said release slots and said cutting aperture.

4. The orthopaedic reamer of claim 2, wherein said plurality of release slots each have a release slot width, said cutting aperture has a cutting aperture width, and said release slot width is approximately equal to said cutting aperture width.

5. The orthopaedic reamer of claim 1, wherein each said notch has a notch width, each said cutting tooth has a cutting tooth width, and said cutting tooth width is wider than said notch width.

6. The orthopaedic reamer of claim 1, wherein said L-shaped opening includes a release slot, a release edge and a cutting aperture therebetween.

7. The orthopaedic reamer of claim 6, including an angle of approximately 90° between said release slot and said cutting aperture.

8. The orthopaedic reamer of claim 6, wherein said release slot has a release slot width, said cutting aperture has a cutting aperture width, and said release slot width is approximately equal to said cutting aperture width.

9. The orthopaedic reamer of claim 6, including an angle of approximately 90° between said release edge and said cutting aperture.

10. A method for providing a cutting feature in an orthopaedic reamer, comprising the steps of:
    providing a generally hemispherical shell;
    fabricating a plurality of generally C-shaped openings in said hemispherical shell thereby producing a plurality of tongues in said hemispherical shell, each said C-shaped opening having a substantially constant width and defining a corresponding said tongue, wherein said fabricating step includes fabricating at least one generally L-shaped opening in said hemispherical shell thereby producing at least one second tongue in said hemispherical shell, each said L-shaped opening having a corresponding said second tongue;
    notching a cutting segment in each said tongue thereby improving the cutting and chip breaking performance of said orthopaedic reamer, each said cutting segment including at least one notch, each said notch having a notch width, each said cutting tooth having a cutting tooth width, said cutting tooth width wider than said notch width; and
    forming said cutting segment in a direction away from said hemispherical shell center.

11. The method of claim 10, wherein said fabricating step includes fabricating in said L-shaped opening a release slot a release edge and a cutting aperture therebetween.

* * * * *